(12) United States Patent
Asano et al.

(10) Patent No.: US 8,414,917 B2
(45) Date of Patent: Apr. 9, 2013

(54) CHEWABLE CAPSULE AND PRODUCTION METHOD THEREOF

(75) Inventors: Yuzo Asano, Yokohama (JP); Kyoichi Oshida, Yamato (JP); Takanori Kobayashi, Fujinomiya (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 749 days.

(21) Appl. No.: 12/422,717

(22) Filed: Apr. 13, 2009

(65) Prior Publication Data

US 2009/0194893 A1 Aug. 6, 2009

Related U.S. Application Data

(62) Division of application No. 10/566,541, filed as application No. PCT/JP2004/011286 on Jul. 30, 2004, now abandoned.

(30) Foreign Application Priority Data

Jul. 31, 2003 (JP) ................................. 2003-284072

(51) Int. Cl.
*A61K 9/48* (2006.01)

(52) U.S. Cl.
USPC ............. 424/463; 424/478; 426/89; 426/512; 426/576

(58) Field of Classification Search ........................ None
See application file for complete search history.

(56) References Cited

U.S. PATENT DOCUMENTS

| | | | | |
|---|---|---|---|---|
| 3,627,695 | A * | 12/1971 | Scarpelli ........................ | 264/4.3 |
| 4,352,825 | A | 10/1982 | Cherukuri et al. | |
| 4,428,927 | A | 1/1984 | Ebert et al. | |
| 6,258,846 | B1 | 7/2001 | Hermelin et al. | |
| 6,333,047 | B1 | 12/2001 | Katagihara et al. | |
| 7,763,276 | B1 * | 7/2010 | Shodai et al. ................. | 424/456 |
| 2004/0224020 | A1 | 11/2004 | Schoenhard | |

FOREIGN PATENT DOCUMENTS

| | | |
|---|---|---|
| EP | 0374359 A2 | 7/1989 |
| JP | 59190916 | 4/1983 |
| JP | 286735 | 3/1990 |
| JP | 7264995 | 10/1995 |
| JP | 10-273436 | * 10/1998 |
| JP | 10273436 | 10/1998 |
| JP | 10310519 | 11/1998 |
| JP | 11266804 | 10/1999 |
| JP | 2000136127 | 5/2000 |
| JP | 200189362 | 4/2001 |
| JP | 2001122770 | 5/2001 |
| JP | 2001161306 | 6/2001 |
| JP | 2001278786 | 10/2001 |
| JP | 2002154949 | 5/2002 |
| JP | 2004196706 | 7/2004 |
| JP | 1080466 | 4/2008 |

OTHER PUBLICATIONS

Humidity Control, Retrieved online [Jul. 19, 2011], Humidity Control Fives Capsule Process a Dose of Success, Retrieved from URL:<http://www.esmagazine.com/articles/humidity-control-gives-capsule-process-a-dose-of-success>.*
Japanese Patent Office, Japanese Office Action in counterpart Japanese Patent Application No. 2005-512585 issued May 19, 2009, 6 pages.
Indonesian Office Action, Feb. 20, 2008, 9 pages.
Letter from Nadia Am Badar, S.H. of Am Badar & Partners, Mar. 12, 2008, 2 pages.
European Search Report, PCT/JP2004011286, mailed Mar. 28, 2007 (4 pages); Letter from D. du Boisbaudry to Shiga International Patent Office, Mar. 30, 2007, 1 page.
Japanese International Search Report and Written Opinion for PCT/JP2004/011286, published Sep. 28, 2004, 9 pages.

* cited by examiner

*Primary Examiner* — Lezah Roberts
*Assistant Examiner* — Nannette Holloman
(74) *Attorney, Agent, or Firm* — Wood, Herron & Evans, L.L.P.

(57) ABSTRACT

This chewable capsule has an encapsulating shell and a filling contained within the encapsulating shell, in which outer diameter of the above encapsulating shell ranges from 14 mm to 25 mm, and mass of the above encapsulating shell ranges from 10% to 20% of the total mass of the chewable capsule, the quantity of the above filling contained within the above encapsulating shell ranges from 1400 mg to 3000 mg, and gelatin is contained in the above encapsulating shell.

1 Claim, 1 Drawing Sheet

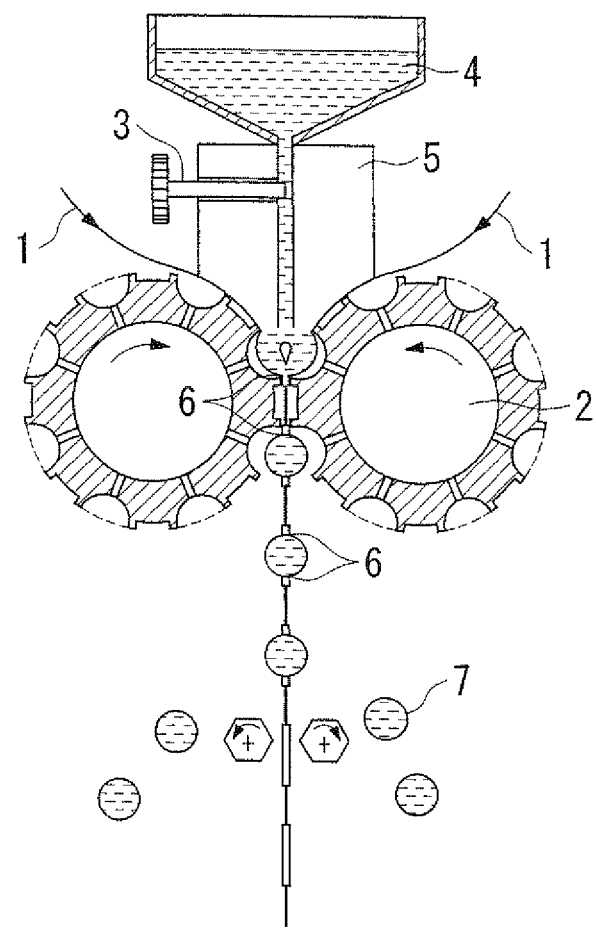

US 8,414,917 B2

CHEWABLE CAPSULE AND PRODUCTION METHOD THEREOF

CROSS-REFERENCE TO RELATED APPLICATIONS

This application is a divisional of pending U.S. patent application Ser. No. 10/566,541 entitled "Chewable Capsule and Production Method Thereof", filed Jan. 27, 2006, which is a U.S. National Phase of PCT/JP2004/011286, filed Jul. 30, 2004, which claims priority to Japanese application No. 2003-284072, filed Jul. 31, 2003, the disclosures of which are hereby incorporated by reference herein.

TECHNICAL FIELD

The present invention relates to a capsule which is suitable for chewing to eat, known as a chewable soft capsule and a production method thereof.

Priority is claimed on Japanese Patent Application No. 2003-284072, filed Jul. 31, 2003, the content of which is incorporated herein by reference.

BACKGROUND ART

As conventional technology with respect to soft capsules which, contain gelatin as a component of an encapsulating shell, or production methods thereof, for example, the following patent documents 1 to 5 are known.

Patent document 1: Japanese Unexamined Patent Application, First Publication No. 2001-89362

Patent document 2: Japanese Unexamined Patent Application, First Publication No. H10-273436

Patent document 3: Japanese Unexamined Patent Application, First Publication No. 2001-161306

Patent document 4: Japanese Unexamined Patent Application, First Publication No. 2000-136127

Patent document 5: Japanese Unexamined Patent Application, First Publication No. H11-266804

Patent document 1 (Film-Covered Granular Substance and Production Method Thereof. SANSEI-IYAKU Co., Ltd.) discloses reduction, of adherance of capsules to each other by precipitating saccharides, such as axylitol contained in the gelatin shell. In Example 1, a method for producing a soft capsule by molding a solution of a packing material which contains gelatin into the shape of a capsule, while filling it with a filling, and solidifying it, and thereafter drying it with rotating, is disclosed.

Patent document 2 (Chewable Soft Capsule, TOKAI CAPSULE Co., Ltd.) discloses blending a plasticizer into a gelatin shell to soften it and blending a crystalline cellulose into reduce adhering of capsules to each other.

Patent document 3 (Process for Producing Gelatin Capsule which Excels in Palatability, EZAKI GLYCO Co., Ltd.) discloses giving a good flavor to a soft capsule by blending an emulsified flavour highly efficiently into a gelatin shell.

Patent document 4 (Rapidly Soluble Soft Capsule, SANSEI-IYAKU Co., Ltd.) discloses a soft capsule having a 15% to 80% of water content in the soft encapsulating shell, and 10% to 70% of soft encapsulating shell mass to total mass of the soft capsule, the soft encapsulating shell of which dissolves very rapidly.

Patent document 5 (Royal Jelly Oily Suspension and Rroyal Jelly Capsule, SANSEI-IYAKU Co., Ltd.) discloses a royal jelly oily suspension in which discoloration is controlled, and a royal jelly soft capsule which is filled with 450 mg of the royal jelly oily suspension as filling and sealed.

Moreover, the following patent document 6 (Hyperlithuria-Disease-Prophylactic Remedy, MORINAGA MILK INDUSTRY Co., Ltd.) discloses a hyperlithuria-disease-prophylactic remedy which contains a substance having 20 carbon, atoms or a derivative thereof, and a mono unsaturated fatty acid having 22 carbon atoms or a derivative thereof as an active ingredient. An encapsulated formulation is illustrated as an example of a dosing form.

Patent document 6: Japanese Unexamined Patent Application, First Publication No. 2001-278786

In order to produce a chew able capsule which is chewed to be eaten, it is necessary that the shell of the capsule be soft so that it can be crunched, and that the capsule be large so that it cannot be swallowed wholly. In addition, it is also important that the content be plentiful and palatable upon being eaten.

However, it is difficult to produce a capsule having such a form, and this goal has not yet been realized. For example, in a conventional soft capsule, it has been difficult to mold a capsule to be relatively large so that it cannot be swallowed, while maintaining physical properties such as hardness, etc., so that it can be crunched. Moreover, if the quantity of the content is increased, then it is likely to cause a self-weight deformation or a self-weight disintegration during production.

The present invention is made under these circumstances, and it is an object of the present invention to provide a capsule which is suitable for chewing to be eaten, and a process for producing such a capsule.

DISCLOSURE OF THE INVENTION

As a result of researching thoroughly in order to solve the above problems, the inventors of the present invention have found that it is possible to produce a capsule which is large, having a large amount of the filling, a soft shell, and good chewing performance, by adopting the following constitution, thereby completing the present invention.

That is, the chewable capsule of the present invention includes an encapsulating shell and a filling contained in the encapsulating shell, and is characterized by having the following properties (a), (b), (c), and (d):

(a) The outer diameter of the encapsulating shell ranges from 14 mm to 25 mm, (b) The mass of the encapsulating shell ranges from 10% to 20% of the total, mass of the capsule.

(c) The quantity of the content contained in the encapsulating shell ranges from 1400 mg to 3000 mg, (d) The encapsulating shell contains gelatin.

The above encapsulating shell preferably contains glycerin in an amount of 30 to 200 mass parts and a crystal precipitating agent in an amount of 1 to 200 mass parts, per 100 mass parts of gelatin.

Preferably, at least a part of the above crystal precipitating agent is exposed to a surface of the shell as a crystal.

Preferably, the above content is a liquid oleophilic substance having a viscosity of not more than 2 Pa·s at 25° C.

Preferably, the above content contains one or more selected from the group consisting of an animal-or-vegetable oil, a phospholipid, and a ceramide.

Alternatively, the above content preferably contains one or more selected from the group consisting of a monounsaturated fatty acid having 20 carbon atoms and/or a derivative thereof, and one or more selected from the group consisting of a mono unsaturated fatty acid having 22 carbon atoms and/or a derivative thereof.

A process for producing the chewable capsule of the present invention includes: a step of molding a capsule-like molded product with a shell material liquid which contains gelatin, and a step of drying the molded product, in which in said step of drying, a first drying for 10 to 12 hours is performed in an atmosphere in which humidity is controlled to be within a range of ±5% and temperature is controlled to be within a range of ±2° C. with respect to first conditions of a humidity of 30% to 50% and a temperature of 20° C. to 30° C., respectively. After the first drying, aging for 2 to 3 hours is performed in an atmosphere in which humidity is controlled to be within a range of 70%±5% and temperature is controlled to be within a range of 25° C.±2° C., and after the aging, a second drying for 35 to 70 hours is performed in an atmosphere in which humidity is controlled to be within a range of ±5% and a temperature is controlled to be within a range of ±2° C. with respect to second conditions of a humidity of 30% to 50% and temperature of 20° C. to 30° C., respectively.

In accordance with the present invention, a chewable capsule which has a size large enough so that the capsule cannot be swallowed wholly, a high hardness but thin shell, easiness of chewing, and tastiness upon being eaten can be obtained.

In accordance with the process for producing a chewable capsule of the present invention, it is possible to produce a high-quality chewable capsule which is large, thin and soft in its shell, and capable of preventing self-weight deformation and self-weight disintegration but has a large amount of the content, by drying it under specific conditions after molding.

The chewable capsule of the present invention has a large outer diameter and a low percentage of the shell mass to total mass of the capsule. Because the shell is thin, the shell dissolves rapidly in the mouth, thereby causing no feeling of remaining shell. In addition, it has a size which makes it easy to eat with the fingers.

Because the shape is of a capsule (i.e., double structure), it is possible to fill it with a filling larger than those of a gummi candy or tablet sweet, etc. Because the filling is covered with a shell, the filling is not substantially oxidized. The effect of protecting the filling is high, and storage stability is excellent.

If crystalline xylitol is exposed to the capsule surface, then cooling feeling will spread in the mouth in a flash when the capsule is eaten. Moreover, adhering between capsules can be prevented, even if the capsules are stored, at a high temperature. They excel in storage stability.

If the viscosity of the content is not more than 2 Pa·s at 25° C., then flowability of the content is excellent, and the content in the capsule is likely to spread in the mouth when it is eaten.

BRIEF DESCRIPTION OF THE DRAWINGS

FIG. 1 is a schematic view showing an example of the rotary type soft capsule filling apparatus suitably used in the Example of the present invention.

BEST MODE FOR CARRYING OUT THE INVENTION

In the present invention, the exterior shape of the encapsulating shell is not particularly limited. For example, it can be molded to have various shapes, such as an approximately spherical shape, a spherical and an ellipse, or an approximate cube, approximate parallelopipedon, etc. A spherical shape or approximately spherical shape is preferable.

The value of the outer diameter of the encapsulating shell in this specification is the greater axis of the capsule, and for example, it can be measured with rulers, such as slide calipers. Moreover, in the case in which the capsule is spherical, it can be also measured by general methods, such as volume conversion.

The outer diameter of the encapsulating shell of the chewable capsule of the present invention ranges from 14 mm to 25 mm. By setting the diameter to be within this range, excellent feeling at the time of consumption can be obtained, such as easiness to eat, easiness to chew, and excellent spreadability (diffusibility) in the mouth when eating.

The percentage of mass of the encapsulating shell to the total, mass of the capsule ranges from 10% to 20%. If the percentage is less than the above range, then there is a possibility that breaking strength may be insufficient, or the content may leak when storing under high temperature or change of ambient temperature. Moreover, if the percentage exceeds the above range, then feeling of melting in the month may deteriorate. Moreover, as the percentage increases, the capsule tends to be less crunchable. Moreover, if the percentage is too large or too small, then it will lose balance with quantity of the content, and as a result, comfortable feeling when eating becomes insufficiently obtainable. The amount of the filling contained in the encapsulating shell is within a range of 1400 mg to 3000 mg. In order to balance the encapsulating shell with the amount of the filling thereof so that tasty feeling when eating can be obtained when the capsule is crunched, the amount of the filling is preferably within the above range. If the amount of the filling exceeds the above range, then it becomes difficult to chew the capsule.

<Encapsulating Shell>

As a composition of the encapsulating shell, gelatin which is a base material for forming the encapsulating shell is contained as an essential ingredient. The gelatin may be one which is derived from any of cow, pig, chicken, and fish. Moreover, the production method thereof may be any method, such as an alkali extracting method or acid extracting method, etc., and the jelly strength etc., of the gelatin is not limited.

It is preferable to blend glycerin as a plasticizer apart from the base material. The blending amount of glycerin into an encapsulating shell is preferably 30 to 200 mass parts to 100 mass parts of gelatin, and more preferably 50 to 100 mass parts. If the blending amount of glycerin is too much or too little, then processability when molding capsules deteriorates, resulting in no comfortable feeling of chewing. Moreover, as the blending amount of glycerin increases, the capsules are more likely to adhere to each other.

It is preferable to blend a crystal precipitating agent in the encapsulating shell. The blending amount of the crystal precipitating agent preferably ranges from 1 to 200 mass parts to 100 mass parts of gelatin, and more preferably 1 to 50 mass parts. As the blending amount of crystal precipitating agent increases, cooling feeling obtained when eating the capsule becomes better, and adherance among capsules becomes infrequent. However, if the blending amount of the crystal precipitating agent is too much, then processability when molding capsules will become worse.

In the chewable capsule of the present invention, it is preferable that at least a part of the crystal precipitating agent which is blended into the encapsulating shell precipitate as a crystal to be exposed to the encapsulating shell surface. As for the state that the precipitant of the crystal precipitating agent is exposed, a state that the above precipitant (crystal) is adhered to the outer surface of the encapsulating shell may be, or a state that a part of the precipitating agent is embedded in the encapsulating shell may be.

As a preferable example of a crystal precipitating agent, sugar alcohols, such as xylitol, erythritol, trehalose, and D-sorbitol, are exemplary. Among these, xylitol is particularly preferable, because it excels in properties, such as precipitating performance of crystal, cooling feeling, and degree of sweetness, etc.

An encapsulating shell may suitably contain flavoring material, such as sweetener, etc. As a sweetener, for example, artificial sweeteners, such as a suclarose, acesulfame potassium, stevia, and aspartame, and a saccharide such as cane sugar or fruit sugar, can be used.

Moreover, in addition to the above components, additives, such as colorants, corrigents, and perfumes, can be included.

<Filling>

The filling is preferably a liquid, and the viscosity at 25° C. is preferably not more than 2·PaS. If it becomes higher than this value, then the spreadability (diffusibility) of the content in the mouth at the time of eating deteriorates. The viscosity is preferably approximately 0.5 Pa·S.

Viscosity of the filling can be adjusted by adding a thickener, if necessary. The thickener is not particularly limited, as long as it can be added to food, but, for example, beeswax, glycerin fatty acid ester, etc. can be used.

Since, if a liquid filling is a hydrophilic substance, the filling is likely to react with gelatin, which is a base material of the encapsulating shell to cause changeover time, the filling is preferably an oleophilic substance. In this specification, "oleophilic substance" indicates a substance which has an oleophilicity (hydrophobicity) of a grade which does not cause effects over time on the encapsulating shell which contains gelatin as a base material.

Although the component of the filling is not particularly limited, oily substances such as an animal or vegetable oil or its powdery suspensions can be used. Specifically, one or more selected from an animal or vegetable oil, phospholipid, and a ceramide are exemplary. As an example of an animal or vegetable oil, safflower oil, olive oil, fish oil, etc. are exemplary.

Alternatively, as components of the filling, one or more selected from a mo no unsaturated fatty acid having 20 carbon atoms and/or derivative thereof, and one or more selected from a monounsaturated fatty acid having 22 carbon atoms and/or derivative thereof can be preferably used. These are known as examples of active ingredients of hyperlithuria-disease-prophylactic remedies (the above patent document 6). Therefore, a chewable capsule which, contains the above components within the content, can be administered orally to a human or an animal as a preservative curing agent, or a nutritional composition for the use of a dietetic treatment for a lifestyle-related illness of which hyperlithuria is representative.

Specifically, the above monounsaturated fatty acid having 20 carbon atoms and/or derivative thereof and the monounsaturated fatty acid having 22 carbon atoms and/or derivative thereof are icosenoic acids (eicosenoic acid), such as gondoic acid having 20 carbon atoms, gadoleic acid, 5-icosenoic acid, etc., and/or derivative thereof, and a docosenoic acid, such as erucic acid (erucine acid) having 22 carbon atoms, cetoleic acid, and 5-docosenoic acid, etc., and/or derivative thereof.

The monounsaturated fatty acid having 20 carbon atoms and the monounsaturated fatty acid having 22 carbon atoms to be used are not particularly limited, as long as they are acceptable medicinally or as a food. Natural fats and oils having a high content of these long chain monounsaturated fatty acids, such, as shark liver oil, whale oil, cod liver oil, rape oil, mustard oil, cabbage seed oil, jojoba oil, meadowfoam seed oil, etc. can be used alone or in combination. Moreover, it is also possible to use an icosene acid or docosenoic acid which is obtained by extracting and refining these natural, fats and oils through a normal method, for example, fractional distillation, crystallization, solvent extraction, urea clathration, or chromatography. It should be noted that a commercially available gondoin acid or erucic acid (all of these are produced by SIGMA Co., Ltd.) can be used as an easy method.

Derivatives of these long chain monounsaturated fatty acids include derivatives like various esters, in addition to salts of long chain monounsaturated fatty acids. Specifically, a salt with an alkali metal, such as sodium, potassium, etc., or an ester with a lower aliphatic alcohol, such as methanol, ethanol, etc., and mono-, di-, or triglyceride, etc. is exemplary.

As for percentage of the monounsaturated fatty acid having 20 carbon atoms and/or derivative thereof and the monounsaturated fatty acid having 22 carbon atoms and/or derivative thereof, the amount of the monounsaturated fatty acid having 22 carbon atoms and/or derivative thereof is preferably 0.1 to 1.7 mass parts of the amount of the monounsaturated fatty acid having 20 carbon atoms and/or derivative thereof because this percentage excels in preventive and curative effects on lifestyle-related illnesses, of which hyperlithuria is representative, compared to the case in which tire percentage is outside the above range.

In the case of performing an oral administration, effective dosage (so with the case of an oral administration at the time of a dietary cure), an effective dosage is 5 to 400 mg/kg in terms of body weight/day, based on the quantity of the active-ingredient which consists of the mono unsaturated fatty acid with, carbon number 20 or its derivative, and the monounsaturated fatty acid with carbon number 22 or its derivative (referred to as "long chain, monounsaturated fatty acids" below). Therefore, it is preferable to set the content of the long chain monounsaturated fatty acid in the filling contained in the chewable capsule so that an effective dosage can be taken by way of one or a few dosagings. In particular, in the chewable capsule of the present invention, the amount of contents per capsule can be increased, and hence the chewable capsule of the present invention is very much suitable for encapsulating long chain monounsaturated fatty acids, which become more effective as intake increases, for the prevention and cure of a lifestyle-related illness.

Moreover, the contents of the chewable capsule may contain, surface active agents, such as glycerin fatty acid esters and cane sugar fatty acid esters, various hardened oils, and waxes, etc.

Moreover, as other components, suitable additives, such as perfume, sweetener, and colorant, may be contained. As for perfume, various natural or synthetic perfumes can be used, corresponding to purpose. As for sweetener, an artificial sweetener, saccharides, sugar alcohol, etc. can be used. As for a colorant, a synthetic colorant, a natural colorant, etc. can be used.

<Production Method>

The chewable capsule of the present invention can be produced by way of the step of forming a capsule-like molded product using a shell material liquid which contains gelatin, and the step of drying the above molded product.

The method for molding the shell material liquid which contains gelatin into the shape of a capsule is not limited, and various well-known methods can be used. For example, as is disclosed in Japanese Unexamined Patent Application, First Publication No. H10-80466, a method for molding an encapsulating shell using a rotary type automatic soft capsule producing apparatus while providing the filling can be suitably used.

Hereafter, one embodiment of the production method of the chewable capsule of the present invention will be explained. FIG. 1 is a schematic view showing an example of a rotary type automatic soft capsule producing apparatus which is suitably used in this embodiment.

First, the constitutional component of the shell is dissolved into a proper quantity of water to prepare a shell material liquid. If necessary, it is heated to dissolve the mixture uniformly. Since molding becomes difficult if the quantity of gelatin is too large or too small, the quantity of gelatin should be within a range so that the shell material liquid can be molded into a desired shaped.

The quantity of gelatin in the shell material liquid ranges from approximately 20 to 45 mass % and, more preferably ranges from approximately 30 to 40 mass %.

On the other hand, besides this, the filling in a liquid form is prepared.

As shown in FIG. 1, two pieces of shell sheet 1 which is molded into the shape of a belt are sent between a pair of rotating cylindrical metallic dies 2. A fillings 4 are pressed between a pair of the shell sheets 1 by the pump 3 which interlocks with this, while the rotating cylindrical metallic dies 2 are rotated. At this time, the shell sheet 1 is heated by a segment 5 to a temperature suitable for performing heat sealing, and the bonded portion 6 is heat sealed by pressing and contact of gibbous tooth formed on the surface of the rotating cylindrical die 2, thereby producing a capsule like molded product 7.

Although, the method for forming the shell sheet 1 is not particularly limited, the shell sheet 1 in a gel form can be produced by, for example, spreading the shell material liquid into a shape of a sheet, and controlling the temperature so that the gelatin gels.

Next, the resultant capsule molded product 7 is dried to produce a chewable capsule.

In the drying step, first, primary drying is performed, that is, drying for 10 to 12 hours is performed in an atmosphere in which the humidity is controlled to within ±5% and the temperature is controlled to within ±2° C. with respect to the first condition of a range of humidity of 30% to 50% and a temperature of 20 to 30° C., respectively.

The primary drying is preferably performed using a rotating drying method. Here, the rotating drying method is a method that includes putting a non-dried capsule into a hollow and air-permeable container having a bottom (for example, a cylindrical cage), and then flowing dehumidified air into the container, while rotating the container, thereby drying the capsule. Specifically, it can be suitably performed using a rotating air-blowing drying apparatus which is equipped with a container, a means for rotating the container, and a means for blowing air.

After the primary drying is completed, aging is performed for 2 to 3 hours in an atmosphere in which the humidity is controlled to within 70%±5% and the temperature is controlled to within 25° C.±2° C. The aging is preferably performed in a state in which the capsule is stationary placed. A more preferable time for aging is approximately 3 hours.

After the aging is completed, secondary drying is performed, that is, drying for 35 to 70 hours is performed in an atmosphere in which the humidity is controlled to within ±5% and the temperature is controlled to within ±2° C. with respect to the second condition of a range of humidity of 30% to 50% and a temperature of 20 to 30° C. respectively, thereby making a chewable capsule. A more preferable drying time is approximately 40 to 60 hours. The secondary drying is preferably performed using a rotating drying method, similarly to the primary drying.

The water content of the capsule shell immediately after the completion of aging is preferably approximately 10 to 20 mass %, in view of chewability and self-deformation. A more preferable range is 13 to 17 mass %. It should be noted that the water content of the capsule shell can be measured using a drying reduction method.

In accordance with the production method in this embodiment, it is possible to produce a large capsule having a thin, soft shell, which is capable of preventing the self-weight deformation and the self-weight disintegration, and thus chewable capsules of the present invention can be produced at high yield.

Specifically, a conventional and ordinary internally-soft-capsule is ordinary molded into a capsule, and thereafter dried for approximately 20 hours in an atmosphere in which the humidity is 30 to 50% and the temperature is approximately 20 to 30° C.; using a rotating air-blowing drying apparatus. On the other hand, the chewable capsule of the present invention is produced to have an external diameter which is far larger than that of an ordinary internal capsule, and a thin (low percentage of shell) capsule shell so that it can be easily chewed. For this reason, if the chewable capsule of the present invention is produced using a conventional method of finishing in one step of drying, then the capsule will be broken by the self-weight during the rotating drying.

Moreover, in this embodiment, the humidity and the temperature during the primary drying and the second drying are strictly controlled (i.e. the tolerance for temperature control, is ±2° C., and the tolerance for humidity is ±5%), and during this, aging is performed under high humidity (the humidity is approximately 70%). In accordance with this producing process, it is possible to prevent the capsule from being deformed or broken during the rotating drying. Moreover, by performing the aging under the above conditions, the crystals will precipitate efficiently due to the crystal precipitating agent contained in the shell material liquid. Moreover, in order to precipitate crystals of xylitol (i.e. crystal precipitating agent) uniformly on the surface of the capsule, the drying rate should be strictly controlled. In accordance with this embodiment, it is possible to obtain a chewable capsule having a uniform quality, on the surface of which the crystal is precipitated uniformly.

EXAMPLE

The present invention will be explained specifically below, using Examples, but, scope of the present invention is not limited to the following Examples.

Example 1

<Preparation of Capsule Filling>
(a) Main caw material: Cod liver oil, 100 mass parts
(b) Thickener: Yellow beeswax (produced by CERARICA NODA Co., Ltd.), 5.4 mass parts
(c) Perfume: Orange perfume (produced by HASEGAWA KOURYOU Co., Ltd.), 2.2 mass parts
(d) Perfume: 1-menthol (produced by KOBAYASHI KATSURA Co., Ltd.), 0.2 mass parts
(e) Sweetener: suclarose (produced by SAN-EIGEN FFI Co., Ltd.), 0.1 mass parts
(f) Colorant: β-carotin (30%) (produced by SAN-EIGEN FFI Co., Ltd.), 0.02 mass parts First, (a) was heated to approximately 70° C., and (b) was added and dissolved.

After this the mixture was cooled to not higher than 30° C., and (c), (d), (e), and (f) were added and agitated. Thereafter, the resultant mixture was ground and emulsified using a colloid mill, and then subjected to a decompressed defoaming to obtain a uniform solution. The resultant solution (i.e. filling) thus obtained had a viscosity of 1.5 Pa·s at 25° C.

Preparation, of Capsule Shell, Material Liquid>

(a) gelatin, (produced by NIPPI GELATIN INDUSTRY Co., Ltd. (gelatin derived from cow bone, blooms 165-185)): 100 mass parts, (b) glycerin: 70 mass parts, (c) erythritol (produced by Mitsubishi Chemical Foods Co., Ltd.): 10 mass parts, (d) xylite 1 (produced by Towa Chemicals Co., Ltd.: XYLITTO): 3.5 mass parts, (e) suclarose (produced by SAN-EIGEN FFI Co., Ltd.): 2 mass, (f) water: 90 mass parts The above (a) to (f) were stirred to dissolve, with, heating, and thereafter the resultant solution was vacuum-deaerated and filtered to obtain, a uniform solution (capsule shell material liquid).

<Production of a Chewable Capsule>

The filling and the capsule shell material liquid prepared as above were used with a rotary type soft capsule filling apparatus to mold a spherical capsule-molded-product having a mass of capsule filling of 1500 mg.

This was immediately dried, in an air atmosphere in which, the humidity was 50% and the temperature was 25° C. for 10 hours using a rotating type air-blowing drying apparatus (the primary drying). It was controlled, so that the humidity was within a range of 50%±5%, and the temperature was within a range of 25° C.±2° C. Moreover, tire rotating rate of the rotating type air-blowing drying apparatus was set to 10 r.p.m.

Next, the resultant molded product was allowed to stand in an air atmosphere in which the humidity was 70% and the temperature was 25° C. for 3 hours (i.e. aging). It was controlled so that the humidity was within a range of 70%±5%, and the temperature was within a range of 25° C.±2° C.

Then, the resultant molded product was dried in an air atmosphere in which the humidity was 50% and the temperature was 25° C. for 35 hours, using a rotating type air-blowing drying apparatus, thereby obtaining a spherical chewable capsule (tire secondary drying). It was controlled so that, the humidity was within a range of 50%±5%, and the temperature was within a range of 25° C.±2° C. Moreover, the rotating rate of the rotating type air-blowing drying apparatus was set to 15 r.p.m. The water content of the capsule shell immediately after finishing secondary drying was 14 mass %.

The chewable capsule (i.e. spherical chewable soft capsule) thus obtained had an external diameter of the shell (spherical diameter) of 16 mm, a total, mass of 1750 mg, and a mass of the capsule shell of 250 mg (it was approximately 14.3% of the total mass of the capsule).

In this Example, neither self-weight deformation of a capsule nor self-weight disintegration occurred, during the rotating drying. Moreover, on the external surface of the capsule of the resultant chewable capsule, crystals of xylitol were uniformly precipitated, and it turned out that it was a capsule with a high quality.

Example 2

Preparation of a Capsule Filling>

(a) The main raw material: DHA content fish oil, 100 mass parts
(b) Thickener: Yellow beeswax (Produced by CERARICA NODA Co., Ltd.), 2.5 mass parts
(c) Perfume: Lemon perfume (produced by TAKASAGO KOURYOU Co., Ltd.), 2.5 mass parts
(d) Sweetener: Aspartame (produced by AJINOMOTO Co., Ltd.), 0.1 mass parts
(e) Colorant: β-carotin (30%) (produced by SAN-EIGEN FFI Co., Ltd.), 0.02 mass parts First, (a) was heated to approximately 70° C., and (b) was added and dissolved. After this the mixture was cooled to not higher than 30° C., and (c), (d) and (e) were added and agitated. Thereafter, the resultant mixture was ground and emulsified by a colloid mill, and then subjected to decompressed defoaming to obtain a uniform solution. The resultant solution (i.e. filling) thus obtained had a viscosity of 1.5 Pa·s at 25° C.

<Preparation of Capsule Shell Material Liquid>

(a) Gelatin (produced by GELAIS Co., Ltd. (gelatin derived from pig skin, blooms 190 to 220)):
(b) Glycerin: 1.50 mass parts
(c) Trehalose (produced by HAYASHIBARA SHOUJI Co., Ltd.): 10 mass parts
(d) Xylitol (produced by TOWA KASEI Co., Ltd.: XYLITTO): 100 mass parts
(e) Water: 90 mass parts The above (a) to (e) were stirred and dissolved with heating to approximately 70° C., and then the resultant solution was subjected to decompressed defoaming and filtered to obtain a uniform solution (capsule shell material liquid).

<Production of a Chewable Capsule>

Similarly to in Example 1, a capsule molded product having a mass of the capsule filling of 3000 mg was molded, using the filling and the capsule shell material liquid prepared as above.

This was immediately dried similarly to in Example 1 to produce a chewable capsule (a spherical chewable soft capsule). The water content of the capsule shell immediately after finishing the secondary drying was 14 mass %.

The chewable capsule (i.e. a spherical chewable soft capsule) thus obtained had an external diameter of the shell (spherical diameter) of 20 mm, a total mass of 3600 mg, and a mass of the capsule shell being 600 mg (it was approximately 16.7% of the total mass of the capsule). In this Example, neither self-weight deformation of the capsule nor self-weight disintegration occurred during the producing steps. Moreover, on the external surface of the capsule of the resultant chewable capsule, crystals of xylitol were uniformly precipitated, and it turned out that it was a capsule with a high quality.

Test Example

Next, Test Examples are described below.

Test Example 1

In Test Example 1, sample chewable capsules were produced in the same way as in Example 1, with the exception of varying the external diameter (spherical diameter) of the capsule shell within, a range of 10 to 30 mm, as shown in Table 1 below. It should be noted that the shell percentage was standardized at 15% by varying the amount of the filling, corresponding to the spherical diameter.

A sensory test was performed on the resultant samples. The sensory test was performed by 20 panelists, who ate each sample to evaluate 3 items of easiness to eat, easiness to chew, and diffusibility of the filling, through a scoring method, based on the following evaluation scale.

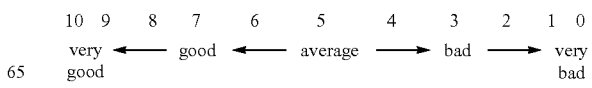

The results are shown in Table 1. The evaluation results of each examination item by 20 panelists are expressed as average±standard deviation.

As to each examination item, distribution analysis and a statistical analysis which, used the PLSD method of Fischer as a Post-hoc test were performed, and evaluation results statistically and significantly not higher than "average" and other than "bad", compared to the other examination samples is regarded as proper. It should be noted that this means that a statistically significant difference is present among the numerals having a letter at the right upper thereof in Table 1, in the case in which the letters are different from each other.

TABLE 1

| Sample No. (Capsule diameter) | Mass of the filling (mg) | Test Items | | |
|---|---|---|---|---|
| | | Easiness to eat | Easiness to chew | Diffusibility of the filling |
| Sample 1 (10 mm) | 1100 | $5.0 \pm 0.9^a$ | $2.1 \pm 0.8^a$ | $1.9 \pm 0.8^a$ |
| Sample 2 (14 mm) | 1400 | $9.9 \pm 0.5^b$ | $7.3 \pm 1.0^b$ | $6.9 \pm 0.9^b$ |
| Sample 3 (20 mm) | 2200 | $9.8 \pm 0.8^b$ | $9.0 \pm 1.0^c$ | $8.8 \pm 1.0^c$ |
| Sample 4 (25 mm) | 3000 | $7.3 \pm 0.8^c$ | $5.4 \pm 1.1^d$ | $6.8 \pm 0.8^b$ |
| Sample 5 (30 mm) | 4500 | $1.9 \pm 0.6^d$ | $1.9 \pm 0.6^a$ | $1.9 \pm 0.6^a$ |

From the results shown in Table 1, it can be seen that in the case in which the external diameter ranges from 1.4 mm to 25 mm, and mass of the filling ranges from 1400 mg to 3000 mg, and results which excel in easiness to eat, easiness to chew, and diffusibility of the filling in the mouth can be obtained.

Test Example 2

Sample chewable capsules were produced in the same way as in Example 1, with the exception of varying the capsule shell percentage within a range of 8% to 25%, as shown in Table 2 and Table 3. It should be noted that the shell percentage was controlled by standardizing the total mass of the capsule 3600 mg and varying the thickness of the capsule shell and the quantity of the filling, as well as standardizing the external diameter (spherical diameter) of the capsule shell 20 mm.

A sensory test was performed on the resultant samples in the same way as in Example 1. The sensory test was performed by 20 panelists, who ate each sample to evaluate 3 items of easiness to crunch, easiness to dissolve in the mouth, and quantity of the filling, similarly to in the method in Test Example 1. The results are shown in Table 2 below.

A test of stability was performed as to the following 3 items.

(1) Destructive strength test: 10 pieces of capsule were dropped from a height of 1 m onto the floor, and evaluated on the degree (degree of dent) of breakage on the surface of the capsule, very good being "A", good although there was a dent being "B", and bad being "F".
(2) Storage-under high temperature test: 10 pieces of capsule were kept for one week in a thermostat held at 40° C. and the state of the capsules was observed. As a result, in the case in which the capsule surface was dried, and there was no adhering among the capsules, no adhering among the capsules was graded "A", in the case in which crystallized portion decreased a little, it is regarded that although there was adhesion, it could be easily broken up into pieces as "B", and capsules adhering to each other which could not be separated by hand was graded "F".
(3) Cycle test: storing in an atmosphere held at 40° C. for 24 hours and storing in an atmosphere held at 5° C. for 24 hours were repeated in 3 cycles, and thereafter adhering of the capsule or the like was observed. The results of the observation were graded such that if the capsule surface was dried, and there was no adhering among the capsules, it was regarded that no adhering was present among the capsules and they were graded "A", in the case in which crystallized portion decreased a little, it is regarded that although there was adhesion, it could be easily broken up into pieces as "B", and adhering to each other which could not be separated by hand were graded "F".

The result of the stability tests is shown in Table 3,

TABLE 2

| Sample No. (Percentage of the shell) | Test Items | | |
|---|---|---|---|
| | Easiness to crunch | Easiness to melt in the mouth of the shell | Quantity of the filling |
| Sample 6 (8%) | $8.9 \pm 0.7^a$ | $8.9 \pm 0.8^a$ | $1.4 \pm 0.5^a$ |
| Sample 7 (10%) | $8.6 \pm 0.9^a$ | $8.6 \pm 1.0^a$ | $7.8 \pm 0.8^b$ |
| Sample 8 (15%) | $8.8 \pm 1.0^a$ | $8.7 \pm 1.2^a$ | $8.8 \pm 1.1^c$ |
| Sample 9 (20%) | $6.7 \pm 0.9^b$ | $6.7 \pm 0.9^b$ | $7.4 \pm 0.8^b$ |
| Sample 10 (25%) | $5.2 \pm 1.0^c$ | $1.7 \pm 0.5^c$ | $1.7 \pm 0.5^a$ |

TABLE 3

| Sample No. (Percentage of the shell) | Test Items | | |
|---|---|---|---|
| | Destructive hardness | Storing under high temperature | Cycle test |
| Sample 6 (8%) | F | F | F |
| Sample 7 (10%) | B | B | B |
| Sample 8 (15%) | A | A | A |
| Sample 9 (20%) | A | A | A |
| Sample 10 (25%) | A | A | A |

From the results shown in Tables 2 and 3, it is clear that if the capsule shell percentage is within the range of 10 to 20%, then it becomes possible to make feeling of eating, such as easiness to crunch, easiness to melt in the month, and quantity of the filling, etc., compatible with stability against external force to the capsule or environmental change.

Test Example 3

The following test was performed regarding preferable blending-rate range of glycerin and xylitol in a gelatin shell. That is, chewable capsules were produced in the same way as in Example 1, with the exception of varying the blending amount of glycerin to 100 mass parts of gelatin within a range of 20 to 250 mass parts, as shown in the following Table 4. At that time, the blending amount of glycerin was standardized at 10 mass parts to 100 mass parts of gelatin.

Moreover, chewable capsules were produced in the same way as in Example 1, with the exception of varying the blending amount of xylitol to 100 mass parts of gelatin within a range of 0.5 to 250 mass parts, as shown in the following Table 5. At that time, the blending amount of glycerin was standardized at 60 mass parts to 100 mass parts of gelatin.

A sensory test and quality judging test were performed on the resultant samples.

The sensory test was performed by 20 panelists, who ate each sample to evaluate the goodness of feeling in chewing as to samples of which glycerin content differed, and the degree of cooling feeling as to samples of which xylitol content differed, similarly to the method in Test Example 1.

In the quality judging test, processing suitability and mutual adhesiveness were evaluated.

(4) The processing suitability was comprehensively evaluated as to easiness to perform actual capsule-molding, from the viewpoints of (1) easiness to cast (i.e. molding of a sheet for forming a capsule), (2) easiness to remove the cast shell sheet from a casting drum, and (3) easiness to perform a heat seal. Samples which, excelled in all of items (1) to (3) were evaluated to be "very good" or "A", samples which dis not excel in one of items (1) to (3) were evaluated to be "good" or "B", samples which did not excel in two of items (1) to (3) were evaluated to be "slightly bad" or "C", and samples which did not excel in any of items (1) to (3) were evaluated to be "bad" or (5) Mutual adhesiveness was evaluated by observing samples which had been stored in an atmosphere held at 40° C. for one week to examine the state of the adhering surface between the capsules, thereby evaluating the external appearance as a product. In the case in which the capsule surface is dry and no adhering among the capsules was present, they were evaluated to be "very good" or "A". In the case in which although the capsule surface was not dry, no adhering among the capsules was present, they were evaluated to be "good" or "B". In the case in which although the capsule surface was adhesive slightly little and a pressing mark could be seen, but no adhering among the capsules was present, they were evaluated to be "average" or "C". In the case in which adhering among the capsules could be seen even if only a little, they were evaluated to be "bad" or "F".

TABLE 4

| | Test Items | | |
|---|---|---|---|
| Sample No. (Blending amount of glycerin) | Processing suitability | Goodness of feeling in chewing | Mutual adhesiveness |
| Sample 11 (20) | C | $1.6 \pm 0.7^a$ | A |
| Sample 12 (30) | B | $5.4 \pm 0.8^b$ | A |
| Sample 13 (60) | A | $6.6 \pm 0.9^c$ | B |
| Sample 14 (100) | B | $9.0 \pm 0.8^d$ | C |
| Sample 15 (200) | B | $8.9 \pm 0.8^d$ | C |
| Sample 16 (250) | F | $6.6 \pm 0.6^c$ | F |

TABLE 5

| | Test Items | | |
|---|---|---|---|
| Sample No. (Blending amount of xylitol) | Processing suitability | Cooling feeling | Mutual adhesiveness |
| Sample 17 (0.5) | A | $1.5 \pm 0.5^a$ | F |
| Sample 18 (1) | A | $7.1 \pm 0.8^b$ | C |
| Sample 19 (10) | A | $7.0 \pm 1.0^b$ | B |
| Sample 20 (100) | A | $9.0 \pm 0.7^c$ | A |
| Sample 21 (200) | B | $8.7 \pm 0.7^c$ | A |
| Sample 22 (250) | F | $9.0 \pm 0.7^c$ | A |

As can be seen in Tables 4 and 5, excellent results were obtained when the blending amount of glycerin was within a range of 30 to 200 mass parts, and the blending amount of xylitol was within a range of 1 to 200 mass parts.

Test Example 4

Chewable capsules were produced in the same way as in Example 1, with the exception of varying the blending amount of beeswax (thickener) in the composition of the filling shown in Example 1 to vary the viscosity of the filling at 25° C. into 6 levels of 0.1, 0.5, 1.0, 2.0, 2.5, and 3.0 Pa·s, as shown in the following Table 6. A sensory test was performed on the resultant samples. The sensory test was performed by 20 panelists, who ate each sample to evaluate the easiness to spread of the filling in the mouth (diffusibility) through a scoring method, similarly to in Test example 1. The results are shown in Table 6 below.

TABLE 6

| Sample No. (Viscosity unit: Pa · s) | Test Item Diffusibility in the mouth |
|---|---|
| Sample 23 (0.1) | $9.0 \pm 0.7^a$ |
| Sample 24 (0.5) | $9.2 \pm 0.7^a$ |
| Sample 25 (1.0) | $8.9 \pm 0.7^a$ |
| Sample 26 (2.0) | $6.9 \pm 0.9^b$ |
| Sample 27 (2.5) | $4.8 \pm 0.8^c$ |
| Sample 28 (3.0) | $1.6 \pm 0.5^d$ |

From the results shown, in Table 6, it is clear that excellent diffusibility can be obtained when tire viscosity of the filling at 25° C. is not higher than 2.0 Pa·s.

Test Example 5

Chewable capsules were produced by changing the drying method into the following 5 methods with respect to each size of capsule, as well as varying the mass of the filling of the capsule into the 6 levels of 1,000 mg, 1,400 mg, 2,000 mg, 2,500 mg, 3,000 mg, and 3,500 mg, in Example 1, in order to examine the preferable drying conditions when producing the chewable capsules. It should be noted that a rotating type air-blowing drying apparatus was used for drying, and the rotating rate was set to 10 r.p.m.

Drying method 1: A method, for drying an ordinary soft capsule (the humidity of 30 to 50%, temperature of 20 to 30° C., and drying time of 20 hours).

Drying method 2: A drying method for drying an ordinary soft capsule in which the drying time is extended (humidity of 30 to 50%, temperature of 20 to 30° C., and drying time of 45 hours).

Drying method 3: A drying method similar to drying method 2, but in which drying is divided into 2 periods between, which aging operation is inserted (humidity of 40±5%, temperature of 25±2° C. and drying time of 45 hours).

Drying method 4: A drying method similar to drying method 2, but in which drying is divided into 2 periods between which aging operation is inserted (humidity of 30 to 50%, temperature of 20 to 30° C., and drying time for the primary drying of 10 hours, and then aging at a humidity of 70% for 3 hours, and thereafter performing the secondary drying for 35 hours under the same conditions as in the primary drying).

Drying method 5: A drying method similar to drying method 4, in which the temperature and humidity are strictly controlled (performing primary drying under conditions in which, the humidity is 40±5% and the temperature is 25±2° C. for 10 hours, and then aging with a humidity of 70±5% for 3 hours, and thereafter performing secondary drying for 35 hours under the same conditions as in the primary drying).

Drying method 6: Drying for 5 hours under conditions in which the humidity is 30%, and the temperature is 31° C., and then allowing to stand for 3 hours under conditions in which the humidity is 80% and the temperature is 28° C., and thereafter drying for 12 hours under conditions in which the humidity is 30% and the temperature is 31° C.

Comprehensive evaluation was performed on the resultant samples, with respect to the self-weight deformation, the self-weight disintegration, and the precipitation state of xylitol crystals. Samples having no problems as a product as to all of the above evaluation items were evaluated "A". Samples which had no problems as a product as to most of the above evaluation items, but have problems as to one of the above evaluation items were evaluated "B". Samples which had no problems as a product as to the above evaluation items, but have problems as to two of the above evaluation items axe evaluated to be "C". The samples which are the level having problems as a product as to at least one of the above evaluation items are evaluated to be "F". In the evaluation items, evaluation results other than "F" are judged to be proper as a product.

TABLE 7

| | Test Items | | | | | |
|---|---|---|---|---|---|---|
| | Drying method 1 | Drying method 2 | Drying method 3 | Drying method 4 | Drying method 5 | Drying method 6 |
| Sample 29 (1,000 mg) | F | F | C | B | A | B |
| Sample 30 (1,400 mg) | F | F | C | B | A | C |
| Sample 31 (2,000 mg) | F | F | F | C | A | F |
| Sample 32 (2,500 mg) | F | F | F | C | A | F |
| Sample 33 (3,000 mg) | F | F | F | F | B | F |
| Sample 34 (3,500 mg) | F | F | F | F | C | F |

According the results shown in Table 7, it is clear that it is possible to produce chewable capsules having a quantity of the filling up to 3,000 mg using the drying method 5, without causing the self-weight deformation and the self-weight disintegration. Moreover, excellent capsules onto which crystals of xylitol uniformly precipitated were obtained.

INDUSTRIAL APPLICABILITY

The present invention can be applied to a chewable capsule, which is utilized for foods, particularly health foods, specified healthcare foods, pharmaceuticals, quasi drugs, etc., known as a chewable soft capsule, and a process for producing such a capsule.

The invention claimed is:

1. A process for producing a chewable capsule, comprising:
   a step of molding an encapsulating shell with a shell material liquid which contains gelatin, and a step of drying said encapsulating shell,
   wherein in said step of drying, first drying for 10 to 12 hours is performed in an atmosphere in which humidity is controlled to be within a range of ±5% and a temperature is controlled to be within a range of ±2° C. with respect to first conditions of a humidity of 30% to 50% and a temperature of 20° C. to 30° C., respectively,
   after said first drying, aging for 2 to 3 hours is performed in an atmosphere in which humidity is controlled to be within a range of 70%±5% and temperature is controlled to be within a range of 25° C.±2° C., and
   after said aging, second drying for 35 to 70 hours is performed in an atmosphere in which humidity is controlled to be within a range of ±5% and temperature is controlled to be within a range of ±2° C. with respect to the second conditions of a humidity of 30% to 50% and a temperature of 20° C. to 30° C., respectively,
   wherein an outer diameter of the encapsulating shell ranges from 14 mm to 25 mm, a mass of the encapsulating shell ranges from 10% to 20% of the total mass of the capsule, a filling contained in the encapsulating shell ranges from 1400 mg to 3000 mg, and a crystal precipitating agent is contained in the encapsulating shell.

* * * * *